US00PP17984P3

(12) United States Plant Patent
Naganuma et al.

(10) Patent No.: US PP17,984 P3
(45) Date of Patent: Sep. 4, 2007

(54) MUSHROOM NAMED 'HOKUTO NT-100'

(50) Latin Name: *Grifola frondosa*
Varietal Denomination: Hokuto NT-100

(75) Inventors: Hitomi Naganuma, Nagano (JP); Eriko Tominaga, Nagano (JP)

(73) Assignee: Hokuto Corporation, Nagano-shi (JP)

( * ) Notice: Subject to any disclaimer, the term of this patent is extended or adjusted under 35 U.S.C. 154(b) by 69 days.

(21) Appl. No.: 11/004,584

(22) Filed: Dec. 6, 2004

(65) Prior Publication Data

US 2006/0162028 P1 Jul. 20, 2006

(51) Int. Cl.
*A01H 15/00* (2006.01)

(52) U.S. Cl. ..... Plt./394

(58) Field of Classification Search ..... Plt./394
See application file for complete search history.

*Primary Examiner*—Kent Bell
*Assistant Examiner*—June Hwu
(74) *Attorney, Agent, or Firm*—Armstrong, Kratz, Quintos, Hanson & Brooks, LLP

(57) ABSTRACT

A new and distinct variety of mushroom, named Hokuto NT-100, is described, which mushroom has the following characteristics: large cap, thick meat, nice consistency, nice taste, uniform growth when cultivated in a facility, and suitable for bottle cultivation. The variety of mushroom named Hokuto NT-100 was developed from mushrooms related to Hokuto MY-95 and Hokuto MY-75, which are registered varieties of a Japanese corporation and a wild variety found in Aomori Prefecture of Japan.

13 Drawing Sheets

BRIEF SUMMARY OF THE INVENTION

The present invention relates to a new and distinct variety of mushroom having the following characteristics: large cap, thick meat, nice consistency, nice taste, uniform growth when cultivated in a facility, and suitable for bottle cultivation. The new variety of mushroom named Hokuto NT-100 was developed from mushrooms related to Hokuto MY-95 and Hokuto MY-75, which are registered varieties of a Japanese corporation, and a wild variety found in Aomori Prefecture of Japan.

Latin name of genus and species and variety denomination of the claimed plant: The Latin name of the genus and species of 'Hokuto NT-100 mushroom' is *Grifola frondosa* (Dicks, ex Fr.) S. F. Gray, this mushroom is generally called "Maitake" in Japan and seems to be called "hen of the woods" in English.

DETAILED DESCRIPTION OF THE INVENTION

The history of the Hokuto NT-100 mushroom in terms of improvement period and the like are set forth in the following chronological list of each stage of variety improvement:

January 1993: By crossing MH18206 amd MH18215, the following three fugal strains were obtained: Hokuto MY-75, Hokuto MY-95 and GD99.

February 1995: Hyphae were obtained from Hokuto MY-75 and GD99.

March 1995: By crossing the hyphae of Hokuto MY-75 and GD99, MH182114 was obtained.

May 1996: From Hokuto MY-95, hyphae were obtained.

June 2000: From MH18284, hyphae were obtained.

August 2000: By crossing the hyphae of MH18284 and MY-95, MH182113 was obtained.

November 2000: From MH182114, hyphae were obtained.

July 2001: From MH182113, hyphae were obtained.

January 2002: By crossing the hyphae of MH182113 and MH182114, a superior variety MH182115 was obtained.

March 2002 to March 2003: Tests were repeated to identify the characteristics of MH182115, and during this time, it was found that bottle cultivation was favorable, and stability, uniformity and differentiability were confirmed. In November 2002, MH182115 was named Hokuto NT-100 and variety improvement was completed. More tests were conducted after that, and characteristics tests were completed in March 2003. The claimed cultivar is stable and reproduces true to type in successive generations of asexual reproduction.

Figure 1:
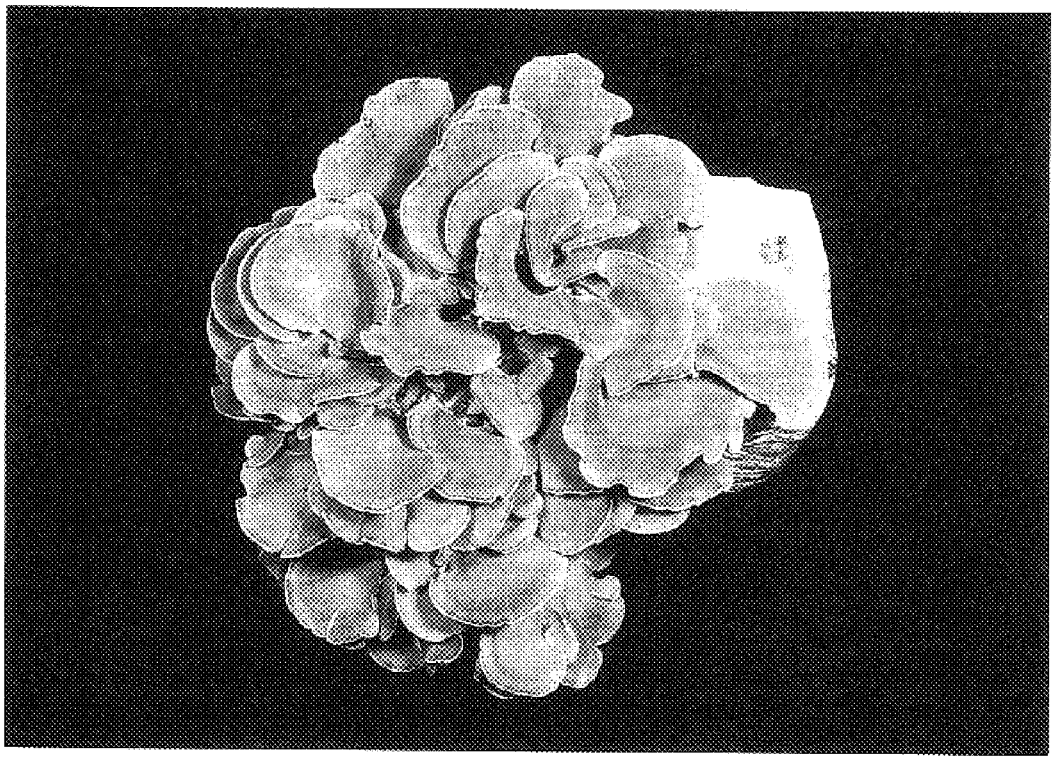
FIG. 1 is a top view of the Hokuto NT-100 mushroom.
Figure 2:
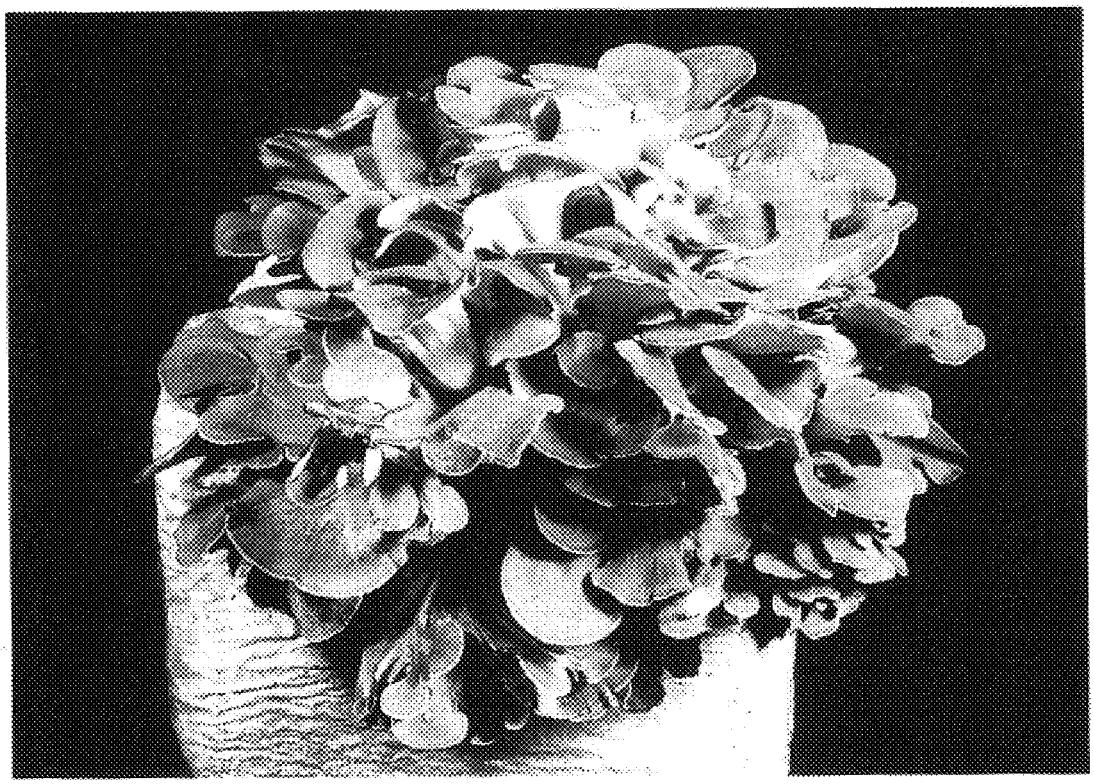
FIG. 2 is an oblique view of the Hokuto NT-100 mushroom.
Figure 3:
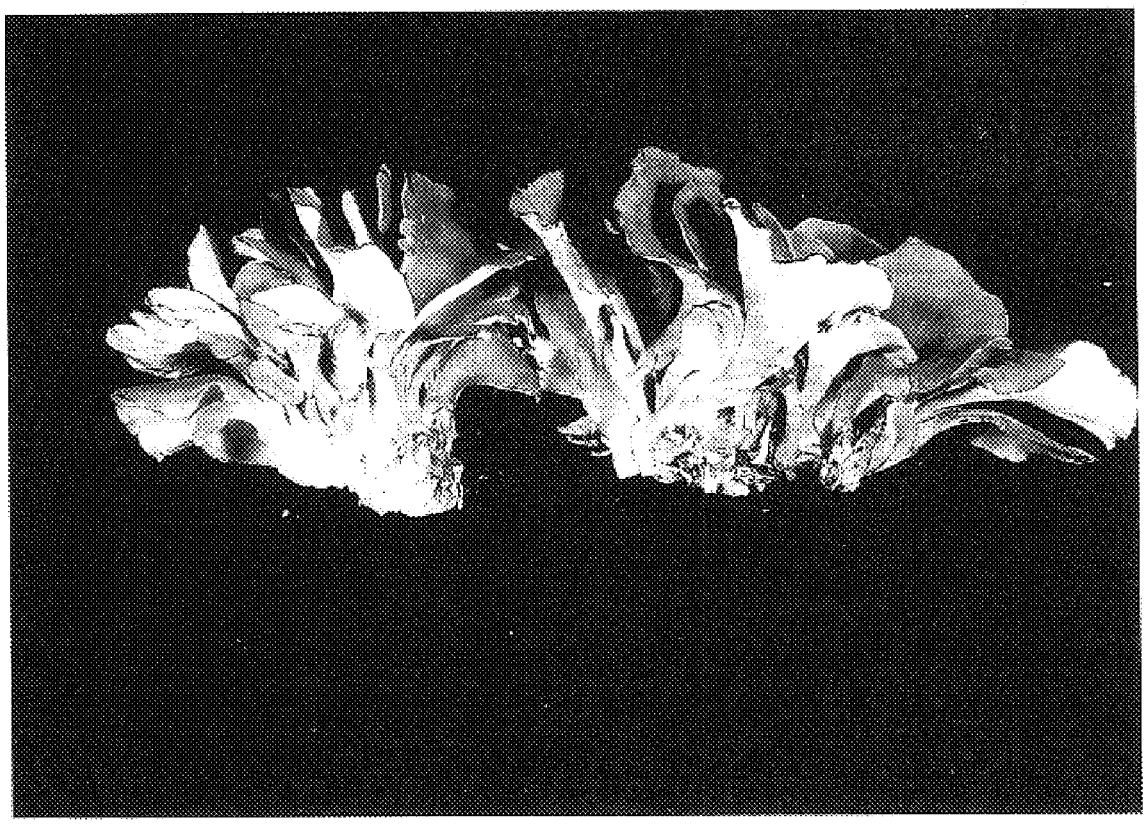
FIG. 3 is a partial side view of the Hokuto NT-100 mushroom.
Figure 4:
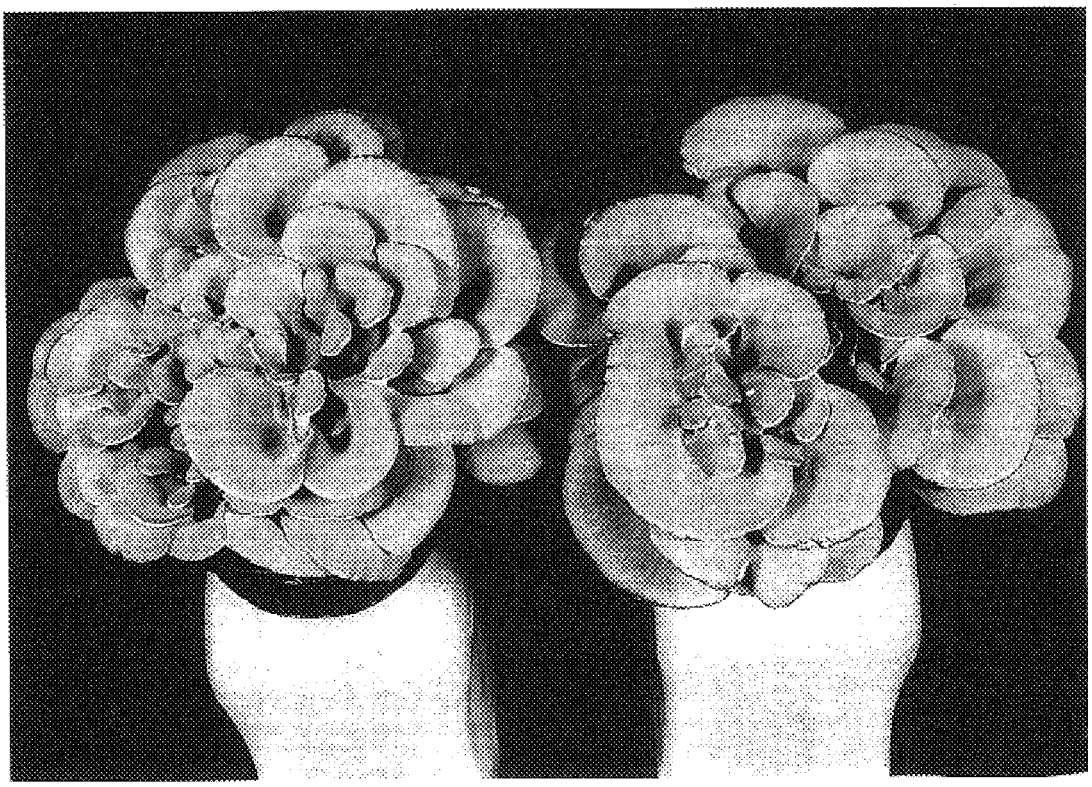
FIG. 4 is an oblique view of the Hokuto NT-100 mushroom in bottle cultivation.
Figure 5:
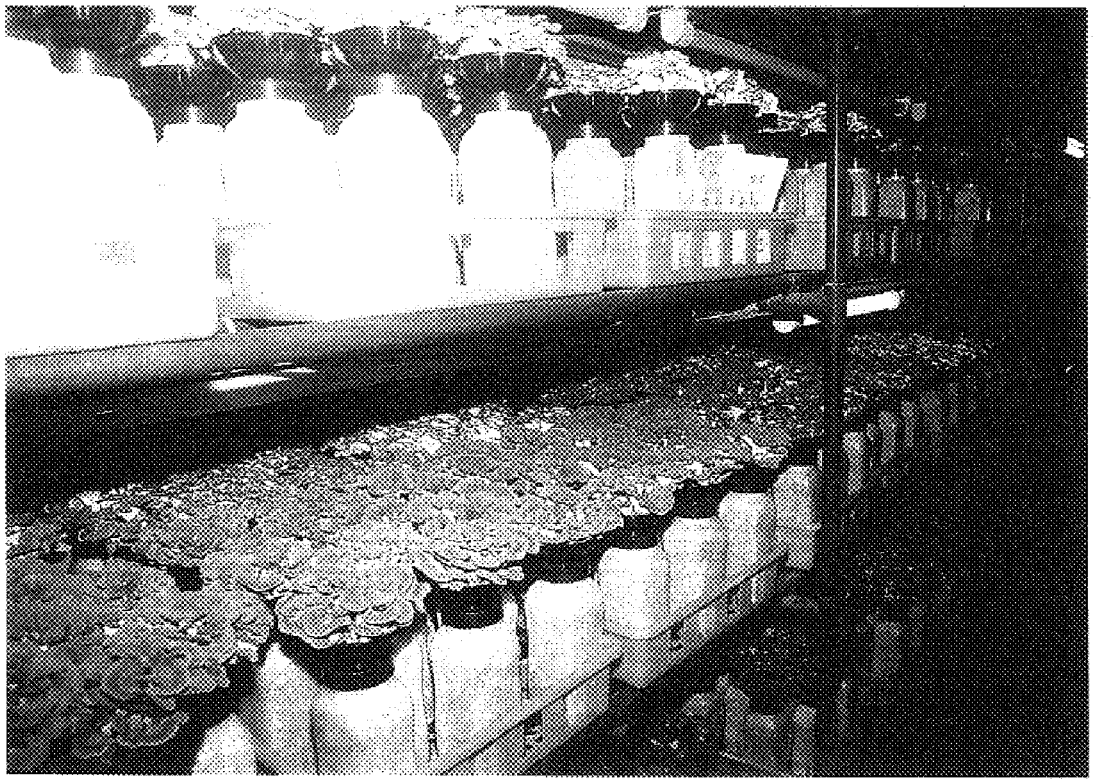
FIG. 5 is a side view of the Hokuto NT-100 mushroom in bottle cultivation.
Figure 6:
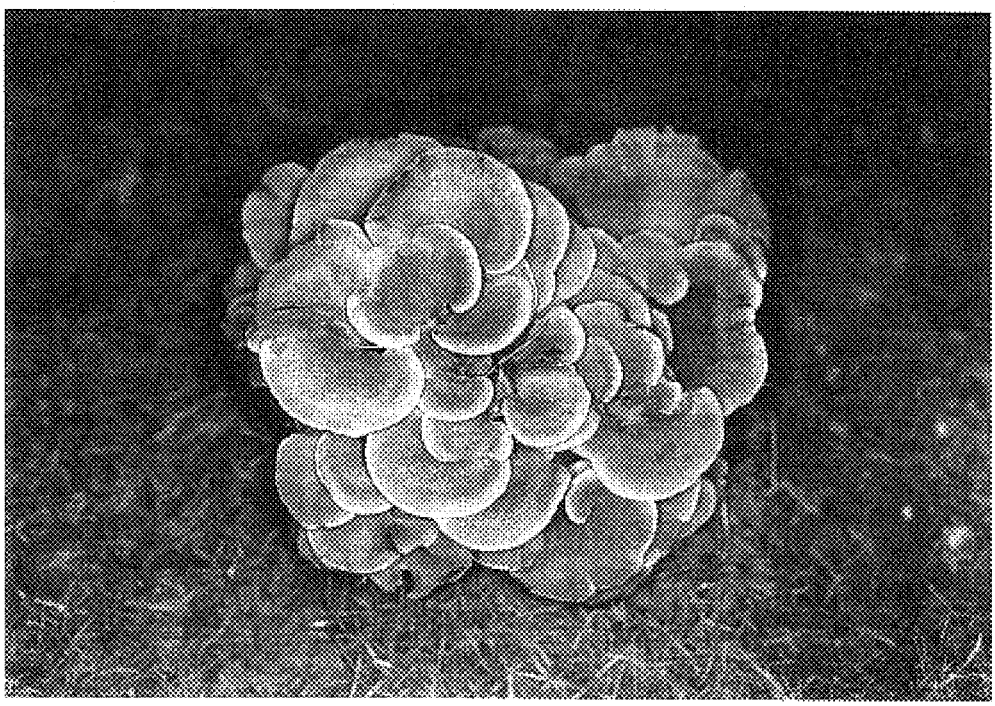
FIG. 6 is a top view of the Hokuto NT-100 mushroom in outdoor cultivation.
Figure 7:
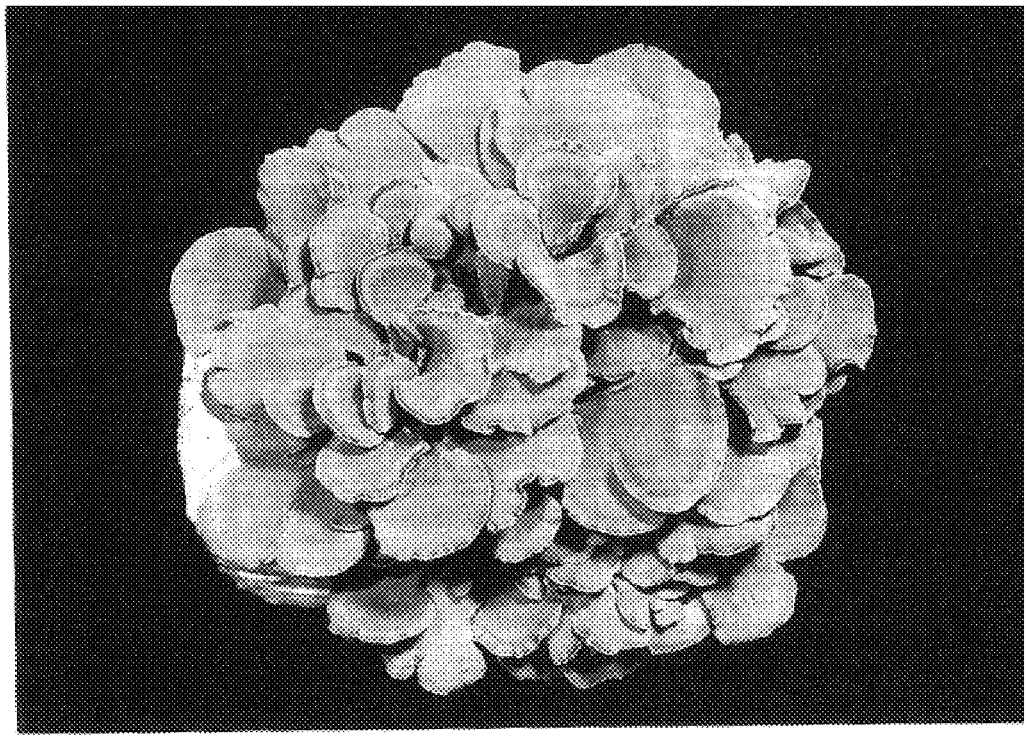
FIG. 7 is a top view of the Hokuto MY-95 mushroom for the purposes of comparison.
Figure 8:
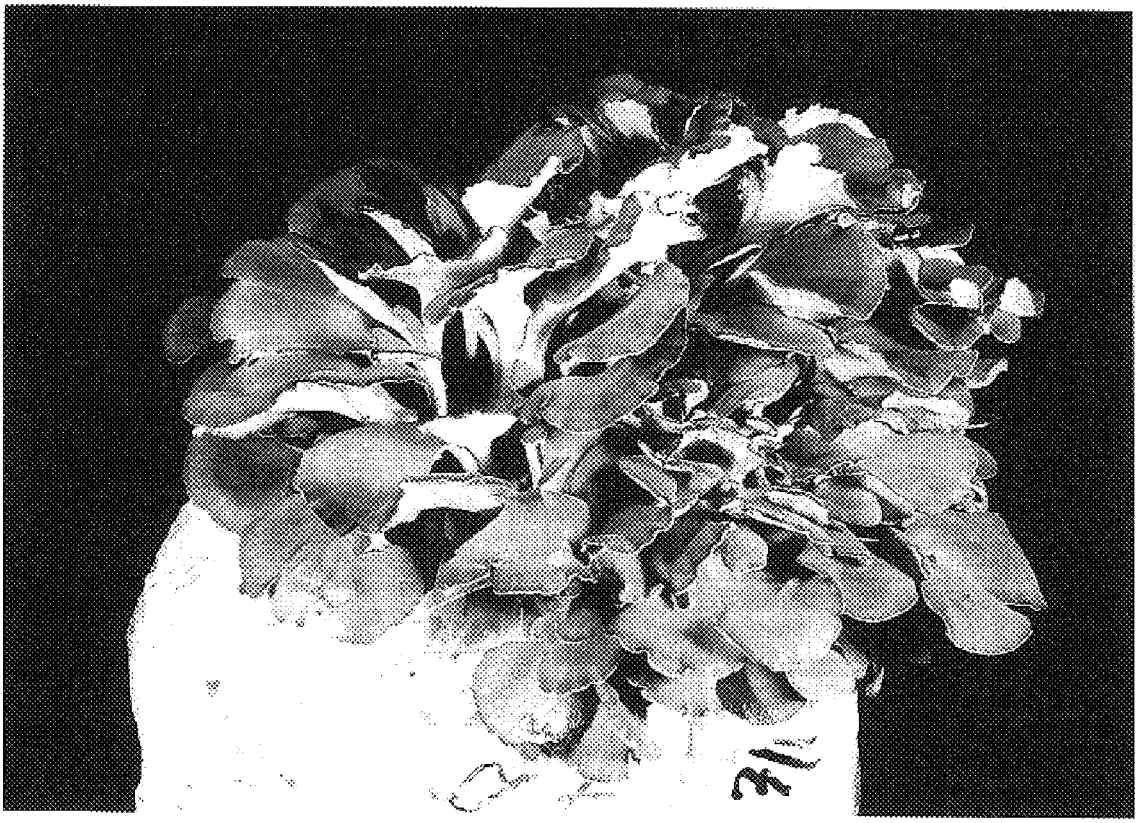
FIG. 8 is a side view of the Hokuto MY-95 mushroom.
Figure 9:
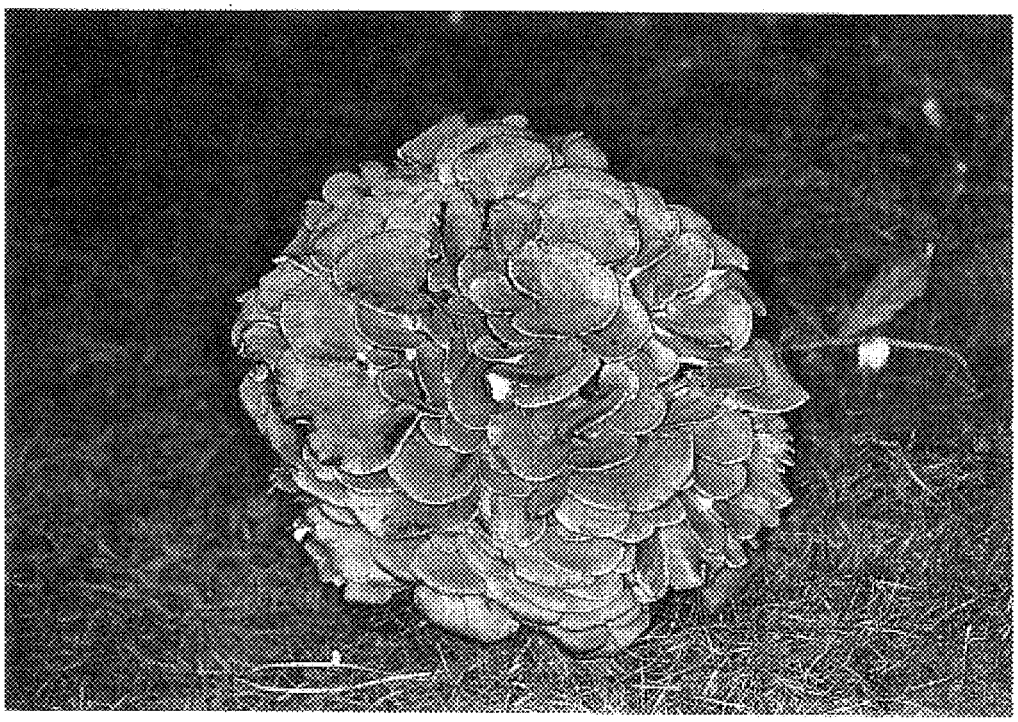
FIG. 9 is a top view of the Hokuto MY-95 mushroom in outdoor cultivation.
Figure 10:
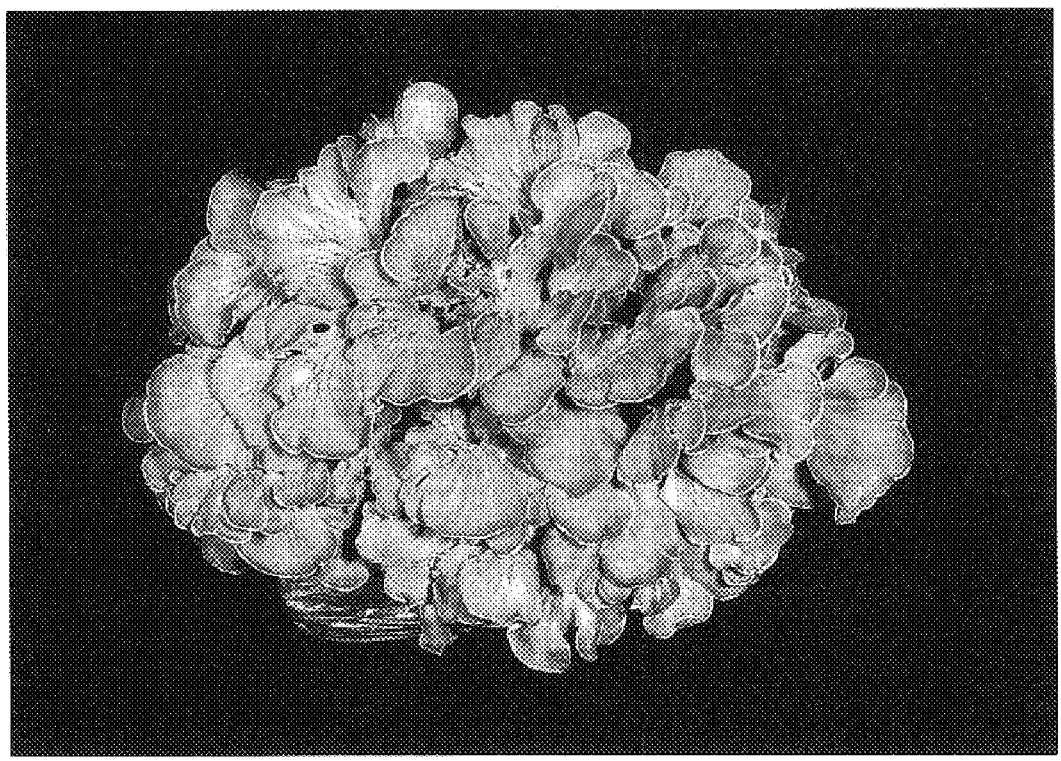
FIG. 10 is a top view of the MH18211 mushroom for the purposes of comparison.
Figure 11:
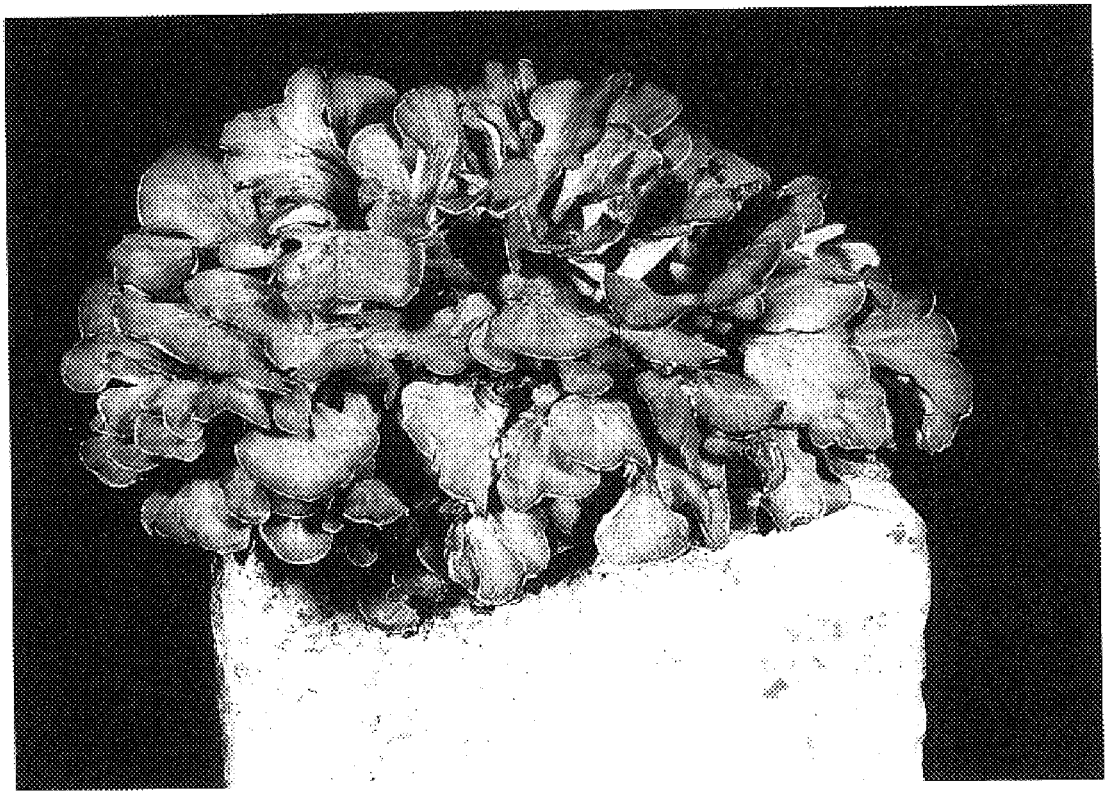
FIG. 11 is a side view of the MH18211 mushroom.
Figure 12:
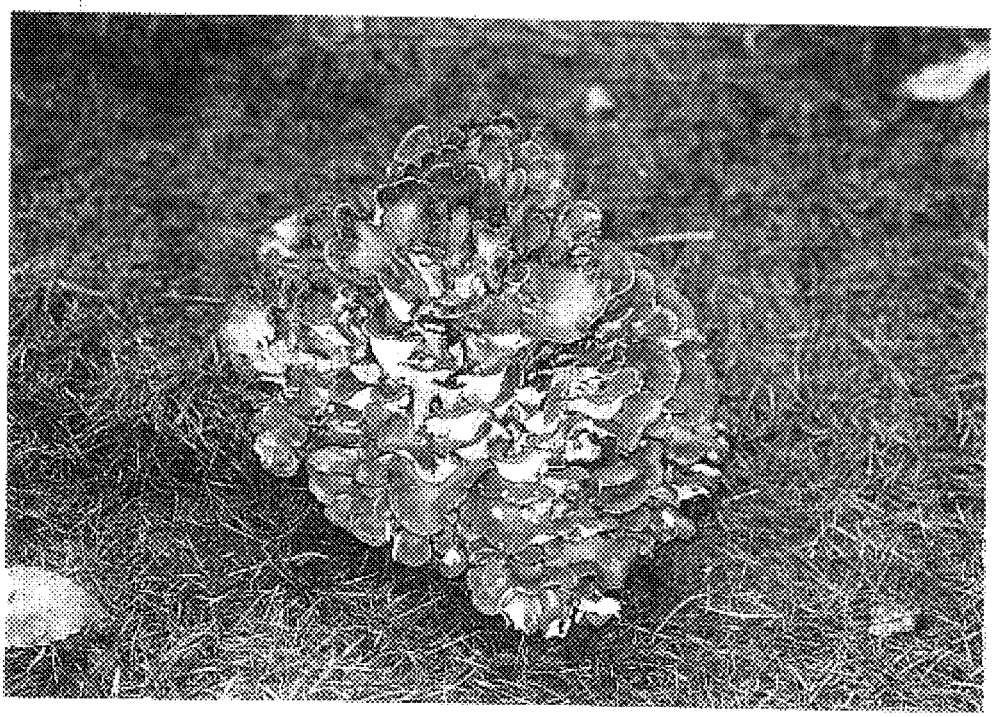
FIG. 12 is a top of the MH18211 mushroom in outdoor cultivation.
Figure 13:
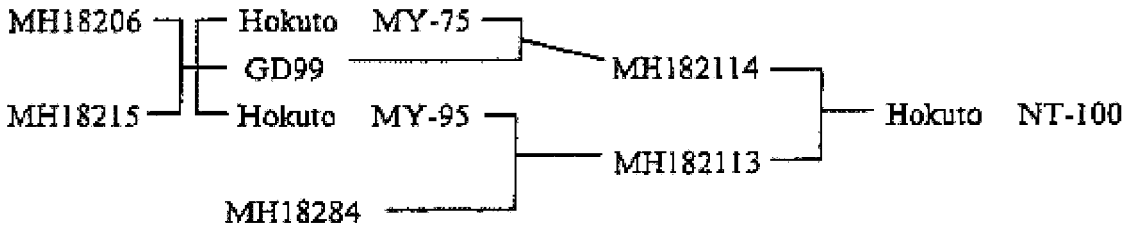
FIG. 13 is a chart showing the system which resulted in the Hokuto NT-100 mushroom.

The system which resulted in the Hokuto NT-100 mushroom is shown in the flow chart of FIG. 13.

The Hokuto NT-100 mushroom has the following characteristics: large cap, thick meat, nice consistency, nice taste, uniform growth when cultivated in a facility, and suitable for bottle cultivation.

The differences between the new variety and its parents are as follows:

The parent varieties are MH182113 and MH182114. Both the parent varieties; and the instant new variety of this application can be defined being different genetically because they show a positive reaction in a dual culture. The new variety is different from MH182113 in cultural characteristics in that the new variety can be yielded numerously and has a different cap color. The new variety differs from MH182114 in yield, cap color and number of cilia on the cap. The differences therebetween are summarized in the following table.

TABLE 1

| Morphological Differences | | | |
|---|---|---|---|
| | Instant New Variety | MH182113 | MH182114 |
| Yield (grams) | 547.1 | 350.0 | 787.8 |
| | | | Dark gray-brown |
| Cilia on the cap | Small | Small | Large |

When Hokuto NT-100 was cultured with commercially available varieties, inhibition zones were seen. In addition, the optimal temperature for hyphal growth was approximately 24 degree C.

The morphological characteristics of Hokuto NT-100 are as follows: at the time of harvest, the cap is fan-shaped or circular; the margin is rounded off; hair is minimal; pore shape is elliptical (Type 1); and pore cross section is uneven. When naturally cultivated, the mode of development is medium and development occurs in September. Experimental data have also shown that the length of time from inoculation to development is 63 days; the optimal development temperatures is 18–20 degree C.; the optimal growth temperature is 17–18 degree C.; and yield is 547.2 g.

With regard to other characteristics, the vitamin $D_2$ content of Hokuto NT-100 was high at 20.6 mg/100 g (international units: 824 IU) according to experimental data.

Some of these characteristics tests for Hokuto NT-100 as compared to similar mushroom varieties Hokuto MY-95 and MH18211 (Mori Sangyo #51) are summarized in the following table:

TABLE 2

| | Characteristic code of filed variety | | | | |
|---|---|---|---|---|---|
| Characteristics | 01 | 02 | 03 | 04 | 05 |
| Genetic | | | | | |
| Dual culture | | | | | |
| Dislike-touch reaction | | | | | |
| Physiology | | | | | |
| Mycelial growth | | | | | |
| Effect of temperature | | | | | |

TABLE 2-continued

| The optimum (° C.) | 22 | 23 | 24 | 25 | 26 |
|---|---|---|---|---|---|
| Growth rate | | | | | |
| 10° C. | | | | | |
| 15° C. | | | | | |
| 20° C. | | | | | |
| 25° C. | | | | | |
| 30° C. | | | | | |
| 35° C. | | | | | |
| Mycelial color | white | | | | |
| shape of the surface of the colony | smooth | tough | | | |
| Shape of colony edge | regular | | | | |
| colony thickness | | | thin | | medium |
| Density of hyphae | | | sparse | | medium |
| Cultivation characteristics | | | | | |
| Capsule formation | | | little | | medium |
| Capsule coloration | Absent | | | | |
| Length of time until fruit body fromation at optimal temperature | <30 | 31~40 | 41~50 | 51~60 | 61~0 |
| Development period (natural cultivation) | | | | | |
| Optimal development temperature (C.) | <15 | 15~20 | 20~29 | >25 | |
| Optimal fruit body growth temperature (C.) | <18 | 18~21 | >21 | | |
| Other | | | | | |
| Budding period (natural cultivation) | | | Early | | inter-mediate |
| Yield (g/bottle) | | | | | |
| Morphology | | | | | |
| Cap | | | | | |
| Size | | | small | | medium |
| Thickness | | | Thin | | medium |
| Notch | Absent | | | | |
| Cross sectional shape | 1 | 2 | 3 | | |
| Face color | W | G-W | D-G | B | D-B |
| Annulus | 1 | 2 | 3 | 4 | |
| Hair | | | fair | | medium |
| Tube | | | | | |
| Shape of tube face | 1 | 2 | 3 | 4 | |
| Unevenness of cross sectional the tip of tube | Absent | | | | |
| Tube position | 1 | 2 | 3 | | |
| Stipe shape | 1 | 2 | 3 | | |

| | Characteristic code of filed variety | | | | Note |
|---|---|---|---|---|---|
| Characteristics | 06 | 07 | 08 | 09 | (Data) |
| Genetic | | | | | |
| Dual culture | | | | | |
| Dislike-touch reaction | | | | + | – |
| Physiology | | | | | |
| Mycelial growth | | | | | |
| Effect of temperature | | | | | |
| The optimum (° C.) | 27 | 28 | 29 | 30 | 24° C. |
| Growth rate | | | | | |
| 10° C. | | | | | 0.8 |
| 15° C. | | | | | 1.7 |
| 20° C. | | | | | 2.4 |
| 25° C. | | | | | 2.6 |
| 30° C. | | | | | 1.0 |
| 35° C. | | | | | 0.1 |
| Mycelial color | | | | other | white |
| shape of the surface of the colony | | | | other | smooth |
| Shape of colony edge | | | | regular | irregular |
| colony thickness | | thick | | | thick |
| Density of hyphae | | dense | | | sparse |
| Cultivation characteristics | | | | | |

TABLE 2-continued

| | | | | |
|---|---|---|---|---|
| Capsule formation | | much | | medium |
| Capsule coloration | | | present | absent |
| Length of time until fruit body fromation at optimal temperature | >70 | | | 63 days |
| Development period (natural cultivation) | | | | 6 month |
| Optimal development temperature (C.) | | | | 18~20° C. |
| Optimal fruit body growth temperature (C.) | | | | 17~18° C. |
| Other | | | | |
| Budding period (natural cultivation) | | Late | | intermediate |
| Yield (g/bottle) | | | | 547.2 g |
| Morphology | | | | |
| Cap | | | | |
| Size | | large | | 56.4 mm |
| Thickness | | Thick | | 2.6 mm |
| Notch | | | present | Absent |
| Cross sectional shape | | | | type 2 |
| Face color | | | other | dark Brown |
| Annulus | | | other | type 3 |
| Hair | | many | | few |
| Tube | | | | |
| Shape of tube face | | | other | type 1 |
| Unevenness of cross sectional the tip of tube | | | present | present |
| Tube position | | | other | type 3 |
| Stipe shape | | | other | type 2 |

| Characteristics | Code of the similar variety: Hokuto MY-95 | Code of the similar variety: HM18211 |
|---|---|---|
| Genetic | | |
| Dual culture | | |
| Dislike-touch reaction | 09 | 09 |
| Physiology | | |
| Mycelial growth | | |
| Effect of temperature | | |
| The optimum (° C.) | 04 | 05 |
| Growth rate | | |
| 10° C. | 0.9 | 0.8 |
| 15° C. | 1.4 | 1.8 |
| 20° C. | 1.6 | 2.5 |
| 25° C. | 2.0 | 2.9 |
| 30° C. | 1.2 | 2.7 |
| 35° C. | 0.1 | 0.2 |
| Mycelial color | 01 | 01 |
| shape of the surface of the colony | 01 | 01 |
| Shape of colony edge | 01 | 09 |
| colony thickness | 05 | 03 |
| Density of hyphae | 03 | 03 |
| Cultivation characteristics | | |
| Capsule formation | 05 | 05 |
| Capsule coloration | 01 | 09 |
| Length of time until fruit body fromation at optimal temperature | 05 | 06 |
| Development period (natural cultivation) | 6 month | 7 month |
| Optimal development temperature (C.) | 02 | 02 |
| Optimal fruit body growth temperature (C.) | 01 | 01 |
| Other | | |
| Buding period (natural cultivation) | 05 | 05 |
| Yield (g/bottle) | 575.9 g | 338.9 g |

TABLE 2-continued

| | | |
|---|---|---|
| Morphology | | |
| Cap | | |
| Size | 07 | 07 |
| Thickness | 05 | 05 |
| Notch | 01 | 09 |
| Cross sectional shape | 02 | 02 |
| Face color | Grayish brown | Grayish yellow |
| Annulus | 03 | 02 |
| Hair | 03 | 03 |
| Tube | | |
| Shape of tube face | 02 | 01 |
| Unevenness of cross sectional the tip of tube | 09 | 09 |
| Tube position | 03 | 03 |
| Stipe shape | 02 | 01 |

The numbers used to describe the characteristics of the cross-sectional shape, annulus, shape of tube face and the others of the instant new variety are indicative of the morphological types prescribed in the Examination Standard stipulated officially in Japan. Distinguishable characteristics of Hokuto NT-100 are set forth in the following:

When cultured with Hokuto MY-95, an inhibition zone is seen. Hokuto NT-100 is different from Hokuto MY-95 in the following characteristics: optimal growth temperature is 24 and 26 degree C., respectively; meat thickness is thick and regular, respectively; yield is 547.2 and 575.9 g, respectively; cap surface color is dark red and grayish brown, respectively; and pore surface shape is type 1 and 2 prescribed in the Examination Standard officially stipulated in Japan, respectively. When cultured with MH18211, an inhibition zone is seen. Hokuto NT-100 is different from MH18211 in the following characteristics: optimal growth temperature is 24 and 28 degree C., respectively; margin shape is irregular and regular, respectively; meat thickness is thick and regular, respectively; bottom capsule is present and absent, respectively; length of time from inoculation to development is 63 and 73 days, respectively; length of time for natural development is 6 and 7 months, respectively; yield is 547.2 and 338.9 g, respectively; cap gill is present and absent, respectively; cap surface is color dark red and grayish yellow, respectively; annellation type is 3 and 2, respectively; and cross section shape of stipe is type 2 and 1, respectively.

The above comparative test results were based, at least in part, on the following tests where the cultivation conditions under which the above-mentioned characteristic tests were conducted were as follows:

a. Cultivation site: Nagano, Japan.

b. Cultivation period: March 2002 to March 2003.

c. Cultivation methods (location, facility, medium, cultivation mode, scale, etc.). Mushrooms listed in the test results were cultivated using conventional methods in a culture room with 300 containers and a growth room with 300 containers. In the characteristics tests, cultivation was performed using ten bags per block and the cultivation experiment was repeated twice.

The following tests were conducted:

(*1*) *Dual culture.*—Conducted according to the examination standards for mushrooms where characteristics were observed on Difco PDA medium. The strains used were: MH18211 Commercial strain (Mori Sangyo #51). MH182113 mating strain. MH182114 mating strain. MH18284 Wild type. Hokuto MY-75. Hokuto MY-95. MH18212 Commercial strain (Fujimoto sangyou M10). MH18222 Commercial strain (Tochiokimaitake). MH148261 Commercial strain (Tokatiana). With regard to the dislike-touch reaction, the results were as follows where + is present and – is absent.

TABLE 3

| | Hokuto NT-100 |
|---|---|
| Hokuto NT-100 | – |
| MH18211 | + |
| MH182113 | + |
| MH182114 | + |
| MH18284 | + |
| Hokuto MY-75 | + |
| Hokuto MY-95 | + |
| MH18212 | + |
| MH18222 | + |
| MH148261 | + |

(2) *Mycelial growth.*—The growth of Hokuto NT-100 was compared with Hokuto MY-95 and MH18211.

TABLE 4

| temperature (° C.) | 10 | 15 | 20 | 25 | 30 | 35 |
|---|---|---|---|---|---|---|
| Hokuto NT-100 (mm/day) | 0.8 | 1.7 | 2.4 | 2.6 | 1.0 | 0.1 |
| Hokuto MY-95 (mm-day) | 0.9 | 1.4 | 1.6 | 2.0 | 1.2 | 0.1 |
| MH18211 (min/day) | 0.8 | 1.8 | 2.5 | 2.9 | 2.7 | 0.2 |

TABLE 5

| temperature (° C.) | 20 | 22 | 24 | 26 | 28 | 30 | optimum temp. |
|---|---|---|---|---|---|---|---|
| Hokuto NT-100 (mm/day) | 2.3 | 2.5 | 2.6 | 2.5 | 2.1 | 1.3 | 24 |
| Hokuto MY-95 (mm-day) | 1.6 | 1.8 | 2.1 | 2.2 | 2.0 | 1.9 | 26 |
| MH18211 (mm/day) | 2.4 | 2.8 | 3.0 | 3.2 | 3.3 | 3.2 | 28 |

(3) *Characteristics data.*—Cultivation data for Hokuto NT-100 was compared with Hokuto MY-95 and MH18211.

TABLE 6

| Characteristics | Hokuto NT-100 | Hokuto MV-95 |
|---|---|---|
| Capsule formation | Medium | Medium |
| Capsule coloration | Absent | Absent |
| Length of time until fruit body formation at optimal temperature | 60-63 days | 60-63 days |
| Optimal development temperature | 18-21 C. | 18-21 C. |
| Optimal fruit body growth temperature | 17-18 C. | 17-18 C. |
| Development period (natural cultivation) | September | September |
| Yield | 574.2 ± 2.6 g | 575.9 ± 53.8 g |
| Cap size | 56.4 ± 16.5 mm | 43.6 ± 15.8 mm |
| Cap thickness | 2.6 ± 0.4 mm | 2.6 ± 0.5 mm |
| Cap surface color | Dark yellowish red (1910) | Grayish brown (1919) |

TABLE 6-continued

| Characteristics | MH18211 |
|---|---|
| Capsule formation | Medium |
| Capsule coloration | Present |
| Length of time until fruit body formation at optimal temperature | 71-73 days |
| Optimal development temperarure | 18-20 C. |
| Optimal fruit body growth temperature | 17-18 C. |
| Development period (natural cultivation) | September |
| Yield | 338.9 ± 44.7 g |
| Cap size | 45.1 ± 10.9 mm |
| Cap thickness | 2.6 ± 0.5 mm |
| Cap surface color | Grayish yellow (2212) |

(4) *Temperature data.*—Data for the optimum development temperature of Hokuto NT-100 was determined using conventional cultivation methods where fungal development was monitored at different temperatures, the results being as follows:

TABLE 7

Primordium formation at each development temperature

| Development temperature (C.) | Hokuto NT-100 |
|---|---|
| <15 | Primordium formation occurred 61 days after inoculation |
| 16-20 | Primordium formation occurred 56 days after inoculation |
| 21-25 | Low pigmentation on the culture medium surface |
| >25 | No budding |

As shown in Table 7, while primordium formation occurred at temperatures below 20° C., when considering cultivation style and productivity, earlier primordium formation is desirable. Therefore temperatures between 16 and 20° C. were suitable, and, in this temperature range, development was most favorable at 18–20° C.

(4) Vitamin D2 Content.

The vitamin D2 content in the fruit body was measured with HPLC and the results were as follows:

TABLE 8

| | Hokuto NT-100 | Hokuto MY-95 | HM18211 |
|---|---|---|---|
| The vitamine D2(μg/100 g) | 20.6 | 15.6 | 7.1 |
| The vitamine D2(IU/100 g) | 824.0 | 624.0 | 280.0 |

With regard to asexual reproduction of the subject mushroom:

(1) The fungal strains in question are preserved at 5° C. on agar slant culture (agar medium) and continuously cultivated once a year.

(2) The medium is a potato dextrose agar culture (PDA) made of 200 grams of potato, 20 grams of glucose, and 15 grams of agar so as to have a pH value of 5.5 in 1 liter of distilled water.

(3) The cultivation of strains is carried out by picking out mycelial fragment from the fungal strains preserved in (1) mentioned above and put on the medium of (2). Then, the strains are cultivated at about 25° C. for 14 days. After bacterial threads of the strains preserved, the strains are displanted to an incubation medium.

In a case of preserving the strains once again, the strains thus cultivated may be restored to the process (1) above.

The characteristic colors of parts of the instant new variety are recited herein based on Japan Color Standard for Horticultural Plant (JHS Color Chart).

It is claimed:

1. A new and distinct variety of mushroom, substantially as described and illustrated herein.

* * * * *

Crossbreeding system